(12) United States Patent
Callne

(10) Patent No.: US 7,112,061 B2
(45) Date of Patent: Sep. 26, 2006

(54) DENTAL ARTICULATOR

(76) Inventor: Lars Callne, 1744 Arbolita La., Fallbrook, CA (US) 92028

( * ) Notice: Subject to any disclaimer, the term of this patent is extended or adjusted under 35 U.S.C. 154(b) by 0 days.

(21) Appl. No.: 11/066,509

(22) Filed: Feb. 24, 2005

(65) Prior Publication Data

US 2006/0188838 A1    Aug. 24, 2006

(51) Int. Cl.
  *A61C 11/00* (2006.01)
(52) U.S. Cl. .............. 433/64; 433/49; 433/54; 433/57
(58) Field of Classification Search ........... 433/61, 433/62, 63, 64, 54, 49, 57
  See application file for complete search history.

(56) References Cited

U.S. PATENT DOCUMENTS

| | | | |
|---|---|---|---|
| 2,688,800 A | 9/1954 | Gerber | |
| 3,466,750 A | 9/1969 | Timberlake et al. | |
| 3,590,487 A * | 7/1971 | Guichet | 433/62 |
| 4,045,873 A | 9/1977 | Burnett | |
| 4,175,325 A | 11/1979 | Beckwith | |
| 4,382,787 A | 5/1983 | Huffman | |
| 4,417,873 A * | 11/1983 | Kulas | 433/57 |
| 4,533,323 A * | 8/1985 | Huffman | 433/60 |
| 4,548,581 A * | 10/1985 | Huffman | 433/64 |
| 4,556,387 A | 12/1985 | Lee | |
| 4,600,386 A * | 7/1986 | Feinmann | 433/60 |
| 4,734,033 A * | 3/1988 | Huffman | 433/60 |
| 4,797,097 A | 1/1989 | Cohn | |
| 4,865,544 A | 9/1989 | Scruggs | |
| 5,007,829 A * | 4/1991 | Farrell | 433/61 |
| 5,026,282 A | 6/1991 | Koike | |
| 5,057,014 A * | 10/1991 | Zeiser | 433/57 |
| 5,064,372 A * | 11/1991 | Edwardson | 433/66 |
| 5,320,528 A | 6/1994 | Alpern et al. | |
| 5,366,373 A | 11/1994 | Mumolo et al. | |
| 5,385,470 A * | 1/1995 | Polz | 433/57 |
| 5,425,636 A | 6/1995 | Ghim | |
| 5,531,595 A | 7/1996 | Koutavas | |
| 5,533,896 A * | 7/1996 | Federici | 433/64 |
| 5,645,425 A | 7/1997 | Callne | |
| 5,707,233 A * | 1/1998 | Hobo et al. | 433/55 |
| 5,769,634 A | 6/1998 | Choi | |
| 6,299,442 B1 * | 10/2001 | Shiao et al. | 433/64 |
| 6,318,998 B1 * | 11/2001 | Miller | 433/64 |
| 6,382,969 B1 | 5/2002 | Elnajjar | |
| 6,450,809 B1 * | 9/2002 | Iverson | 433/64 |
| 6,485,302 B1 * | 11/2002 | Kim | 433/74 |
| 6,499,999 B1 * | 12/2002 | Van Valey | 433/57 |
| 6,508,646 B1 * | 1/2003 | Pacino et al. | 433/64 |
| 6,558,161 B1 * | 5/2003 | Nagata | 433/57 |

* cited by examiner

*Primary Examiner*—Patricia Bianco
*Assistant Examiner*—Patrick J. Kilkenny
(74) *Attorney, Agent, or Firm*—Calif Tervo Palomar Patent

(57) ABSTRACT

A dental articulator for connecting first and second dental models generally includes upper and lower arms hinging at their rear ends by a hinge. Each arm front end is connected by a coupling to a dental model. Each coupling generally includes a ball, a coupling, a rear socket and a fastener joining the coupling and rear socket such that the socket is movable rotationally, up and down, and side to side on the ball to a selected position. The hinge also provides for movements of the arms mimicking those of a human jaw. The lower arm means for adjusting the height of the hinge. Upper and lower dental models each include a holder of an incisor spacing assembly co-cast into the base. The holders hold an incisor pin for adjusting the vertical spacing between the fronts of the dental models.

10 Claims, 3 Drawing Sheets

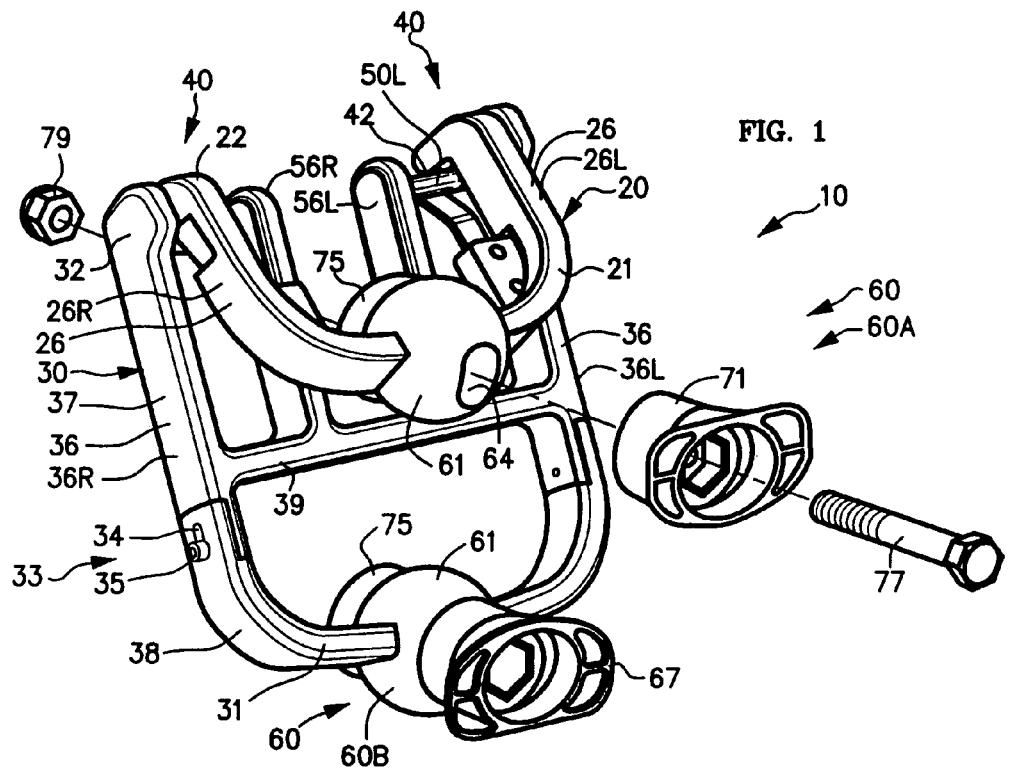
FIG. 1
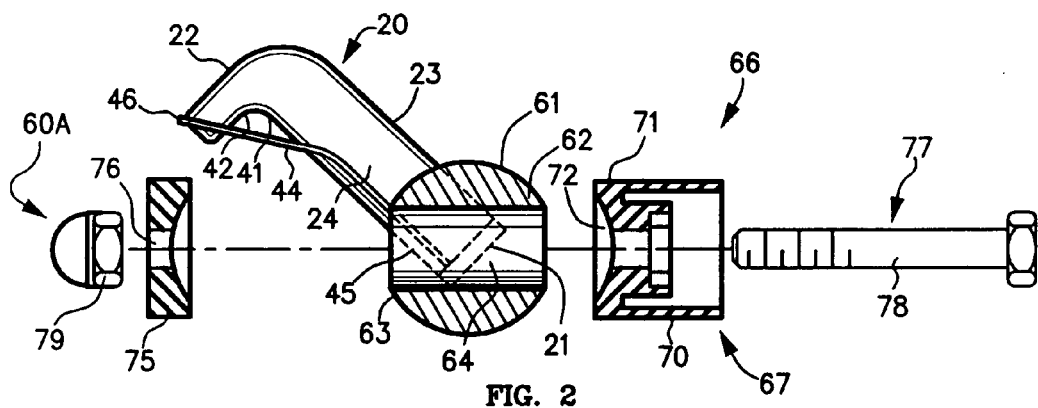
FIG. 2
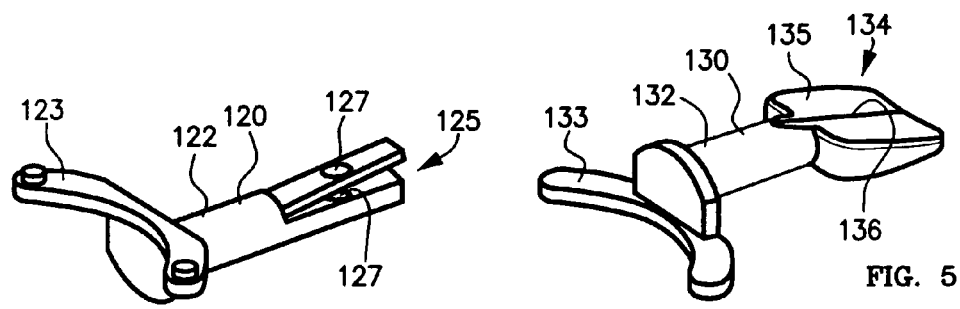
FIG. 4
FIG. 5

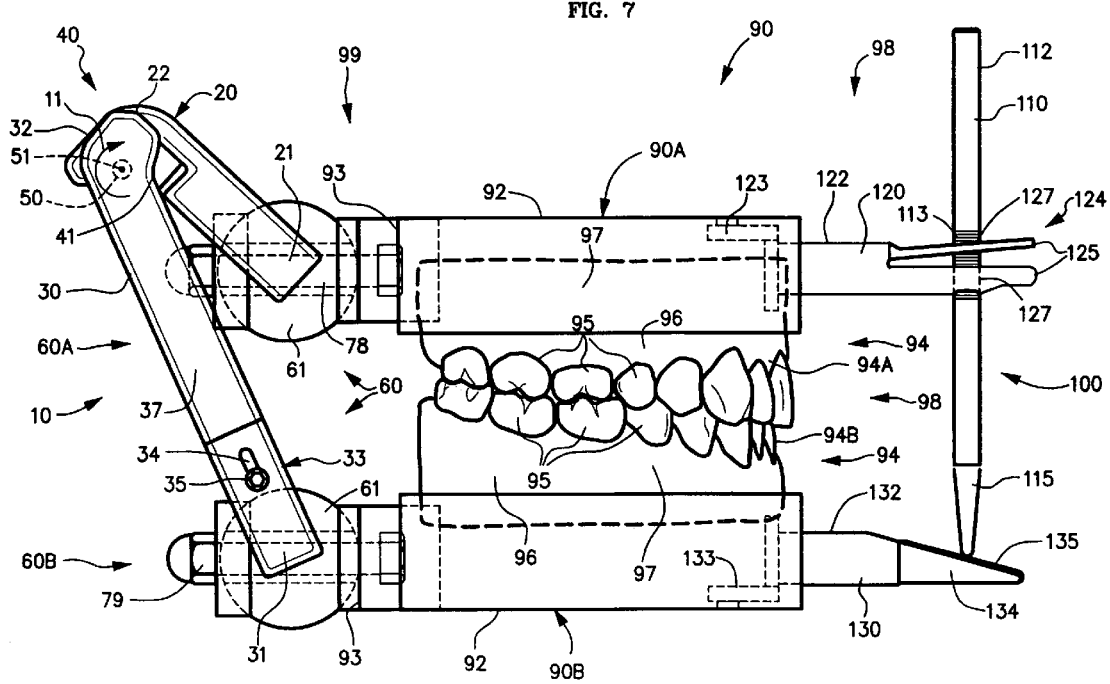

DENTAL ARTICULATOR

FIELD OF THE INVENTION

This invention relates in general to dental articulators, and more specifically involves a dental articulator for directly receiving a dental model.

BACKGROUND OF THE INVENTION

Articulators or correlators for use with a dental model to develop dental prostheses or denture elements have been used for a number of years. In crown and bridge laboratories, typically molds (model formers) made of rubber or silicone, are used to make models. A pourable, hardenable stone (plaster) is poured in the mold to form the base. A tooth die, i.e., a model of a patient's upper or lower teeth and gums, is co-cast in the base, i.e., set partially into the base before the base hardens. The base of the dental model is then mounted to an articulator.

With most articulators, the dental model is attached to the articulator by plastering. After the articulation functions are performed, the dental model is knocked from the articulator. The articulator must then be cleaned of plaster before re-use.

A few articulators are marketed that use methods other than plastering for attaching the dental model to the articulator. These typically use screws or clamps to hold the dental models. These plaster-less articulators are expensive and often require considerable time to align the upper and lower dental models.

Therefore, there has been a need for a dental articulator that directly receives a dental model without requiring additional plastering.

It is further desirable that the articulator easily attaches to the dental model at a desirable longitudinal up/down angle, horizontal side-to-side angle, and lateral tilt angle.

It is further desirable that the articulator provide for selective adjustment of the vertical rear spacing of the mounted dental models after alignment.

It is further desirable that the articulator provide for selective adjustment of the vertical front spacing of the mounted dental models after alignment.

SUMMARY OF THE INVENTION

The invention is a dental articulator for connecting first and second dental models and generally includes upper and lower arms hingly connected at their rear ends by a hinge. Each arm front end is connected by a coupling to a dental model.

Each coupling generally includes a ball, a coupling, a rear socket and a fastener. The ball is connected to the front end of the arm and has a central, longitudinal bore therethrough. The model connector includes a front end adapted for attachment to the dental model and a front socket for receiving the ball. The rear socket receives the rear of the ball. The fastener is disposed in the bore of the ball and fastens the front socket to the rear socket. The fastener is adjustable such that the front socket is movable rotationally, up and down, and side to side on the first ball to a selected position and such that the front socket is fixed in the selected position. The hinge also provides for relative longitudinal, protrusive, and lateral movement of the arms. The lower arm is substantially upright and includes means for adjusting the height of the hinge.

The articulator is combined with a dental model wherein the front end of the connector is co-cast into the base of the dental model. In a preferred embodiment, upper and lower dental models each include a holder of an incisor spacing assembly co-cast into the base. The holders hold an incisor pin for adjusting the vertical spacing between the fronts of the dental models.

Other features and many attendant advantages of the invention will become more apparent upon a reading of the following detailed description together with the drawings wherein like reference numerals refer to like parts throughout.

BRIEF DESCRIPTION OF THE DRAWINGS

FIG. 1 is a top, front, right side, partially-exploded, perspective view of a preferred embodiment of the dental articulator of the invention.

FIG. 2 is an exploded side elevation cross-section view of the upper arm and upper coupling of FIG. 1.

FIG. 4 is a top, front, left side perspective view of an upper holder for an incisor pin.

FIG. 5 is a top, rear, left side perspective view of a lower holder for an incisor pin.

FIG. 7 is a side elevation view of the articulator of FIG. 1 attached to dental models including an incisor pin assembly.

DETAILED DESCRIPTION OF THE INVENTION

Figures 3A, 3B:
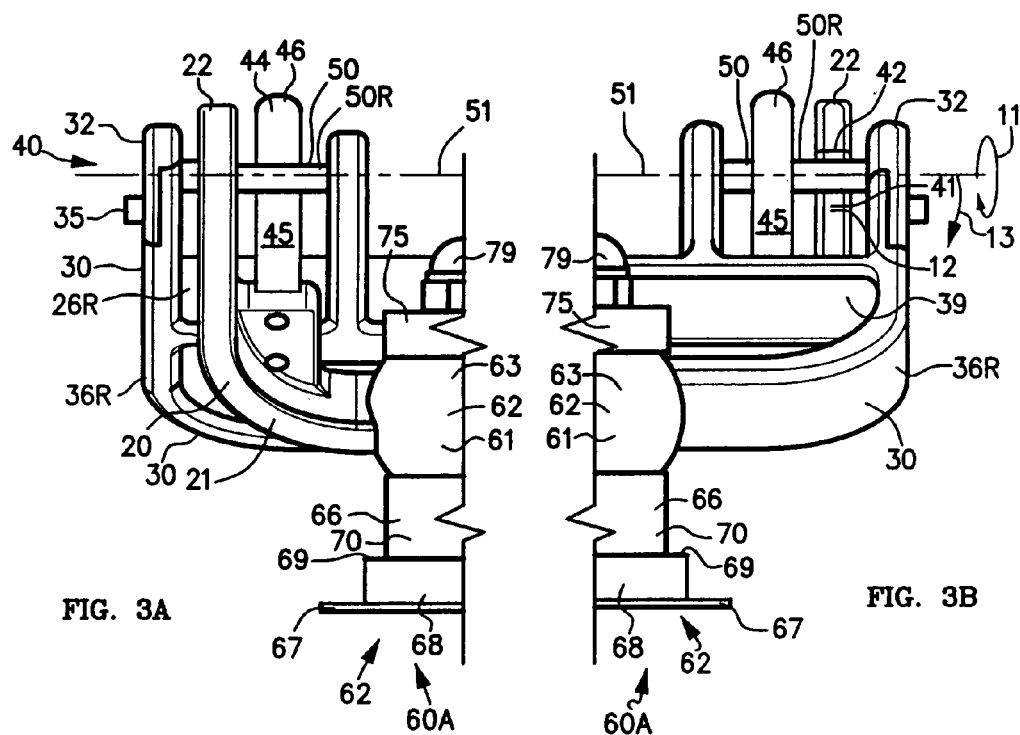
FIG. 3A is a top plan view of the right half of the articulator of FIG. 1 assembled; the left half being a mirror image.
FIG. 3B is a bottom plan view of the right half of the articulator of FIG. 1 assembled; the left half being a mirror image.

Looking first at FIGS. 1 and 7 of the drawing; FIG. 1 is a top, front, right side, partially-exploded, perspective view of a preferred embodiment of the dental articulator 10 of the invention, and FIG. 7 is a side elevation view of articulator 10 of FIG. 1 attached to a dental model 90. Dental model 90 has a front 98 corresponding to the front of a mouth and a rear 99 corresponding to the rear of a mouth. The front/rear direction defines the longitudinal direction. Dental model 90 includes an upper dental model 90A and a lower dental model 90B. Each dental model 90A, 90B includes a base 92 having a rear face 93 and includes a tooth cast 94, such as maxilla cast 94A or mandible cast 94B. Each tooth cast 94 includes gum 96 holding one or more teeth 95. Portions 97 of gum 96 are co-cast in base 92.

Articulator 10 generally includes upper and lower articulating arms 20, 30, hinge means 40 hinges upper and lower arms 20, 30; and couplings 60, such as upper and lower couplings 60A, 60B, coupling upper and lower arms 20, 30 to upper and lower dental models 90A, 90B respectively. Each upper and lower coupling 60A, 60B, includes a ball 61 connected to the front end 21, 31 of its respective upper or lower arm 20, 30.

Further including FIGS. 2, 3A, and 3B; FIG. 2 is an exploded side elevation cross-section view of upper arm 20 and upper coupling 60A; FIG. 3A is a top plan view of the right half of articulator 10 of FIG. 1 assembled; the left half being a mirror image; and FIG. 3B is a bottom plan view of the right half of articulator 10 of FIG. 1 assembled; the left half being a mirror image.

Upper arm 20 has a front end 21, a rear end 22, a bottom 24, and a top 25. Upper arm 20 includes two curved arms 26, left arm 26L and right arm 26R, in a generally U-shaped configuration from the front in top view. Front end 21 is connected to ball 61 of upper coupling 60A. Lower arm 30 has a front end 31 and a rear end 32. Front end 31 is connected to ball 61 of lower coupling 60B. Lower arm 30 includes two arms 36, such as left arm 36L and right arm 36R, in a generally U-shaped configuration in front view. A stabilizing bar 39 joins arms 36L, 36R near their midsections to add stability and strength.

Hinge means 40 hinges rear end 22 of upper arm 20 and rear end 32 of lower arm 30. In the preferred embodiment shown, hinge means 40 includes the following elements. Near the rear end 22 of each curved arm 26 of upper arm 20 is a downward facing, longitudinally oriented, journal receiving surface 41 for receiving a journal 50. With articulator 10 arranged in the typical configuration, journal receiving surface 41 of upper arm 20 is inclined at 28 to 33 degrees (condylar inclination) to simulate the concomitant downward movement with forward movement of the lower jaw in movement of lower arm 30.

The rear ends 32 of left and right lower arms 36L, 36R each support a laterally oriented axle or shaft, such as journal 50, for disposition on journal receiving surfaces 41 of upper arm 20. Journal 50 acts as a hinge pin and defines a hinge axis 51 about which upper and lower arms 20, 30 are pivotable. In the embodiment shown, the medial ends of left and right journals 50L, 50R are supported by left and right auxiliary arms 56L, 56R respectively attached to lower arm 30, such as to stabilizing bar 39. As alternatives, a single journal 50 may extend between rear ends 32, or ends 32 may each cantilever a journal 50, such as left and right journal 50L, 50R.

Laterally spaced and laterally oriented journals 50L, 50R are adapted for disposition on journal receiving surfaces 41 such that: lower arm 30 may hinge about journals 50 relative to upper arm 20 to perform the opening and closing motion of upper and lower dental models 90A, 90B; journals 50 may jointly longitudinally slide along surfaces 41 such that lower arm 30 moves longitudinally relative to upper arm 20 to perform the protrusive movement of dental model 90; and such that journals 50 may independently longitudinally slide on surface 41 such that front end 31 of lower arm 30 moves laterally relative to front end 21 of upper arm 20 to perform the lateral movement of dental model 90. These three movements, hinge 11, protrusive 12 and lateral 13, are indicated in FIG. 3B.

The laterally spaced, journal receiving surfaces 41 each terminate rearward at a rear stop 42 that functions as longitudinal restraining means for restraining rearward longitudinal travel of journals 50.

Journal biasing means includes cantilevered springs 44 on upper arm 20. Springs 44 retain journals 50 on surfaces 41 and bias journals 50 toward a predetermined position, such as toward the centric occlusion position with journals 50 adjacent rear stop 42 as shown in FIG. 7 wherein journals 50 are at the rear of surface 41 wherein dental models 90A, 90B are in standard engaged position. Springs 44 have a front end 45 connected to upper arm 20 near front end 21 and a rear end 46. Preferably, rear ends 46 of springs 44 are rearward of rear end 22 of upper arm 20 so that, upon joining upper and lower arms 20, 30, at hinge 40, journals 50 push springs 44 downward and away from rear stops 42 so that journals 50 can be disposed on surface 41. Pressure from springs 44 serves as forward longitudinal restraining means for restraining forward longitudinal travel of journals 50. Other longitudinal restraining means could be used. For example, front stops on surface 41 may stop forward travel or springs 44 may have upward protrusions that function as front and rear stops.

The length of upper arm 20 and lower arm 30 are such that, in the centric occlusion position as seen in FIG. 7, hinge axis 51 is located approximately in the relative location of a person's jaw axis, that is, above the plane of the teeth opening and, likely, above teeth 95 of upper dental model 90A. Articulator 10 includes hinge height adjustment means 33 for selectively adjusting the height of hinge axis 51 in the centric position. The height could be made adjustable in any one of many manners. In the embodiment shown, lower arm 30 is substantially upright and the length of lower arm 30 is adjustable. Lower arm 30 includes an upper portion 37 slidingly attached to a lower portion 38. Lower portion 38 of each arm 36 includes an elongate through-slot 34 for receiving the shank of a screw 35. Upper portion 37 of each arm 36 includes a threaded bore, not shown, for receiving screw 35. Preferably, slot 34 is sufficiently long to adjust the height by at least 3–5 millimeters. This makes a corresponding adjustment to the separation of the rear teeth of teeth 95 of upper and lower models 90A, 90B. Articulator 10 is shown with hinge axis 51 in the lowest position.

Couplings 60, such as upper and lower couplings 60A, 60B, couple upper and lower arms 20, 30 to upper and lower dental models 90A, 90B respectively. Each coupling 60 generally includes a ball 61, a model connector 66, a rear socket 75, and a fastener 77. Each upper and lower ball 61 is connected to the front end 21, 31 of its respective upper or lower arm 20, 30. Ball 61 includes a front 62, a rear 63 and a central, longitudinal bore 64 therethrough.

Model connector 66 generally includes a front end 67 adapted for attachment to dental model 90 and a rear end 71. Front end 67 includes a stand-off flange portion 69 and an anchor 68. Rear end 71 includes a front socket 72 for receiving front 62 of ball 61. Rear socket 75, adapted for receiving rear 63 of ball 61, includes a bore 76. Fastener 77 includes a tension member, such as a threaded member, such as bolt 78, and an adjustment member, such as nut 79. Bolt 78 has a head anchored in model connector 66 and a shaft for disposition through front socket 72, through bore 64 of ball 61, and through bore 76 of rear socket 75. Nut 79 attaches to bolt 78 to hold sockets 72, 75 on ball 61. Nut 79 is selectively adjustable between a first or loose position wherein front socket 72 is movable rotationally, up and down, and side to side to a selected position on front 62 of ball 61 and a second or tensioned position wherein front socket 72 is fixed in the selected position on ball 61. Bore 64 and fastener 77 are adapted such that, in the loose position, front socket 72 is movable rotationally, up and down, and side to side on ball 61. In the embodiment shown, this is accomplished by having bore 64 of ball 61 considerably larger than the diameter of bolt 78. Other manners may be used.

One problem of prior art devices is the tendency for the dental model to move from the desired position when the adjustment mechanism is being tightened. This problem is ameliorated or cured in the instant invention by fastener 77 being in the center of sockets 72, 75 such that, upon tightening, very little torsion is applied to sockets 72, 75 so they do not move on ball 60. Additionally, couplings 60A, 60B include friction enhancing means on ball 60 and/or sockets 72, 75 for enhancing friction between sockets 72, 75 and ball 60 such that sockets 72, 75 do not move on ball 60 during tightening of fastener 77. Friction enhancing means may be any suitable means, such as a rough surface or a sticky surface. A rough or serrated outer edge on socket 72, 75, or a sticky surface, such as a thin coat of sticky rubber or the like, applied to socket 72, 75 has been found to prevent movement upon tightening.

Looking again at FIG. 7, upper dental model 90A includes an upper holder 120 for incisor pin 110 and lower dental model 90B includes a lower holder 130 for incisor pin 110 of an incisor spacing assembly 100. Incisor spacing assembly 100 includes incisor pin 110, upper holder 120, and lower holder 130 and provides means for centering the fronts 98 of the dental models 90A, 90B and adjusting the vertical spacing between bases 92 of upper and lower dental models 90A, 90B and consequently, the vertical spacing between the front teeth 95 of dental model 90.

Figure 6:
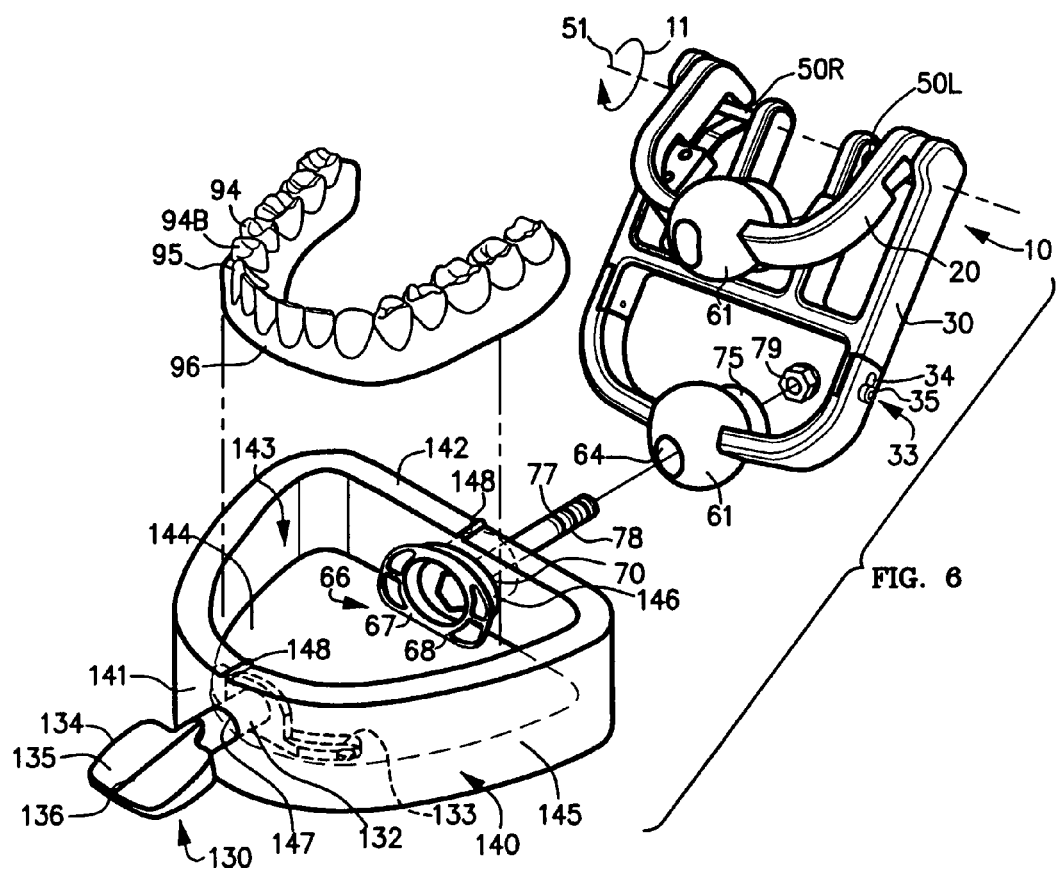
FIG. 6 is a partially exploded, front, top, left side perspective view illustrating the making of a lower dental model.

Further including FIGS. 4, 5, and 6: FIG. 4 is a top, front, left side perspective view of an upper holder 120 for an incisor pin 110; FIG. 5 is a top, rear, left side perspective view of a lower holder 130 for incisor pin 110; and FIG. 6 is a partially exploded, front, top, left side perspective view illustrating the making of lower dental model 90B in a model former, such as mold 140.

Mold 140 is used to cast upper or lower dental models 90A, 90B. Mold 140 has a front 141 and a rear 142 and includes a floor 144 and a surrounding, upright periphery wall 145 defining an interior space 143 for receiving plaster. The rear of periphery wall 145 includes means, such as a bore 146 therethrough, for disposition therethrough of model connector 66. The front of periphery wall 145 includes means, such as bore 147 therethrough, for disposition therethrough of a holder 120, 130 of incisor pin assembly 100. Mold 140 may include means, such as a slit 148 from the top of wall 145 to one or both bores 146, 147 to facilitate removal of a cast dental model 90A, 90B from mold 90. During molding, the resiliency of mold 140 keeps slits 148 from leaking. Alternatively, other means, such as using tape to cover slits 148, may be used to prevent leaking by slits 148.

Upper holder 120 includes a neck 122 for passage through bore 146 of mold 140, an anchor 123 for casting in base 92 and an incisor pin engaging portion 124, such as jaws 125. Lower holder 130 includes a neck 132 for passage through bore 146 of mold 140, an anchor 133 for casting in base 92 and an incisor pin engaging portion, such as table 134. The upper portion 112 of incisor pin 110 is engaged by upper holder 120 and the lower end is engaged by lower holder 130. Preferably, the incisor pin supporting surface 135 of table 134 is slanted downward rear to front, typically at an angle of five to ten degrees, and downward from outer sides to the center, typically at an angle of about fifteen degrees, as to have a center crease or dihedral 136 on the longitudinal axis of the dental model 140.

Incisor pin 110 is an elongate rod with a lower end 115 adapted, such as by being pointed, for centering on dihedral 136. Jaws 125 are spaced and movable between a first position wherein vertical bores 127 through both jaws 125 align and a second position wherein bores 127 do not align such that a shaft, such as pin 110 disposed therethrough is held. Jaws 125 are biased to the non-aligned position. To adjust front vertical spacing of models 90A, 90B, the free ends of jaws 125 are moved to align bores 127, pin 110 is moved to the desired length between upper and lower holder 120, 130. Then jaws 125 are released to hold pin 110. Upper portion 112 of pin 110 includes means, such as a plurality of measured closely vertically spaced circumferential ridges 113, for engaging bores 127 of jaws 125 of upper holder 120 for more precise holding and measurement of adjustment.

As best seen in FIG. 6, lower dental model 90B is made as follows. Model connector 66 of lower coupling 60B is inserted into rear bore 146 of mold 140 such that neck 70 is disposed in bore 146 and anchor 68 is in interior space 143 of mold 140. Lower holder 130 for incisor pin 110 is inserted into front bore 147 in mold 140 such that neck 132 is disposed in bore 147, anchor 133 is disposed in interior space 143 of mold 140 and dihedral 136 is facing upward. A plaster, typically a pourable hardenable stone called "yellow stone" is poured into interior space 143 of mold 140. The lower portion or gum portion 96 of lower teeth die 94B is inserted into the poured stone before the stone has hardened at the proper lateral orientation. After the stone has hardened, the lower dental model 90B is removed from mold 140 and is attached to articulator 10 as seen in FIG. 7. Upper dental model 90A is made in a similar manner with upper holder 120 and model connector 66 of upper coupling 60A co-cast with base 92. Molds come in a variety of sizes to accommodate a variety of teeth dies 94.

As best seen in FIGS. 6 and 7, in the preferred embodiment, the shank of a bolt 78 protrudes rearward from each dental model 90A, 90B such that it can be inserted in bore 64 of ball 61 and facilitates joining of models 90A, 90B with articulator.

From the foregoing description, it is seen that the present invention provides an extremely efficient and reliable coupling for joining an articulator to a dental model. The combination of articulator and dental model provides for adjustment of the front and rear spacing of the models.

Although a particular embodiment of the invention has been illustrated and described, various changes may be made in the form, composition, construction, and arrangement of the parts herein without sacrificing any of its advantages. For example, although, the invention has been illustrated and described using a full dental model, that is using all or nearly all of the teeth in a mouth, the invention is also applicable to smaller models, such as to half or quadrant models. Therefore, it is to be understood that all matter herein is to be interpreted as illustrative and not in any limiting sense, and it is intended to cover in the appended claims such modifications as come within the true spirit and scope of the invention.

I claim:

1. In combination:

a dental articulator including:

an upper arm having a length; said upper arm including:

a front end;

a rear end;

a bottom; and a top;

a lower arm having a length; said lower arm including:

a front end;

a rear end;

a hinge hinging said rear end of said upper arm and said rear end of said lower arm about a hinge axis; said hinge including:

a pair of downward facing, laterally spaced, longitudinally oriented, journal receiving surfaces on said upper arm; and a pair of laterally spaced, laterally oriented journals on said rear end of said lower arm adapted for disposition on said journal receiving surfaces such that: said lower arm may pivot about said journals relative to said upper arm to perform the opening and closing motion of the dental models; said journals may jointly longitudinally slide on said journal receiving surfaces such that said lower arm moves longitudinally relative to said upper arm to perform the protrusive movement of the dental models; and said journals may independently longitudinally slide on said journal receiving surface such that said front end of said lower arm moves laterally relative to said upper arm to perform the lateral movement of the dental model;
   a cantilever spring biasing said pair of journals upward and rearward toward a predetermined position on said journal receiving surfaces; and
an upper coupling including:
   an upper ball connected to said front end of said upper arm; said upper ball including:
      a front;
      a rear; and
      a central, longitudinal bore therethrough;
an upper dental model including:
   an upper teeth die including:
      a tooth portion including:
         one or more teeth; and
      a gum portion;
   an upper model connector including:
      a front end; and
      a rear end including:
         an upper front socket for receiving said front of said upper ball; and
   an upper base cast with said gum portion of said upper teeth die and said front end of said upper model connector embedded therein;
an upper rear socket receiving said rear of said upper ball;
an upper fastener disposed in said bore of said upper ball and connected to said upper front socket and to said upper rear socket so as to compress said upper ball therebetween; said upper fastener being selectively adjustable between a first position wherein said upper front socket is movable rotationally, up and down, and side to side on said upper ball to a selected position and a second position wherein said upper front socket is fixed in the selected position on said upper ball;
a lower coupling including:
   a lower ball connected to said front end of said lower arm; said lower ball including:
      a front;
      a rear; and
      a central, longitudinal bore therethrough; and
a lower dental model including:
   a lower teeth die including:
      a tooth portion including:
         one or more teeth; and
      a gum portion;
   a lower model connector including:
      a front end; and
      a rear end including:
         a lower front socket for receiving said front of said lower ball; and
   a lower base cast with said gum portion of said lower teeth die and said front end of said lower model connector embedded therein;
a lower rear socket receiving said rear of said lower ball;
a lower fastener disposed in said bore of said lower ball and connected to said lower front socket and to said lower rear socket so as to compress said lower ball therebetween; said lower fastener being selectively adjustable between a first position wherein said lower front socket is movable rotationally, up and down, and side to side on said lower ball to a selected position and a second position wherein said lower front socket is fixed in the selected position on said lower ball; and
wherein: said lower arm is approximately twice the length of said upper arm such that the biased predetermined position of said journals approximates the location of the hinge axis of a human jaw relative to said upper teeth.

2. The combination of claim 1 wherein:
said first fastener includes:
   an elongate threaded tension member.

3. The articulator of claim 1 wherein:
said lower arm is substantially upright and includes:
   height adjustment means for adjusting the height of said hinge.

4. The combination of claim 1 wherein:
said upper dental model includes:
   an upper support of an incisor spacing assembly; said upper support including:
      a real portion co-cast in said upper base; and
      a front portion.

5. The combination of claim 4 wherein:
said lower dental model includes:
   a lower support of an incisor spacing assembly; said lower support including:
      a rear portion co-cast in said lower base; and
   a front portion extending forward form said lower base.

6. The combination of claim 5 including:
incisor spacing means supported by said upper and lower supports for adjusting the spacing between the fronts of said dental models.

7. The combination of claim 6 wherein:
said articulator includes:
   height adjustment means for adjusting the height of said hinge.

8. The combination of claim 1 wherein:
said upper ball or said upper rear socket includes friction enhancing means for enhancing friction between said upper ball and said upper rear socket for preventing said upper rear socket from moving on said upper ball during tightening of said upper fastener.

9. The combination of claim 1 wherein:
said upper fastener includes:
   a front end anchored in said upper model connector; and
   a shaft disposed through said upper front socket and through said bore of said upper ball.

10. The combination of claim 1 wherein:
said upper fastener includes:
   a front end anchored in said upper model connector;
   a shaft disposed through said upper front socket and through said bore of said upper ball; and
   a free end; and
said lower fastener includes:
   a front end anchored in said lower model connector;
   a shaft disposed through said lower front socket and through said bore of said upper ball; and
   a free end.

* * * * *